(12) United States Patent
Hauel et al.

(10) Patent No.: US 6,660,764 B2
(45) Date of Patent: Dec. 9, 2003

(54) CARBOXYLIC ACID AMIDES, PHARMACEUTICAL COMPOSITIONS CONTAINING THESE COMPOUNDS, THEIR USE AND THE PREPARATION THEREOF

(75) Inventors: Norbert Hauel, Schemmerhofen (DE); Henning Priepke, Warthausen (DE); Klaus Damm, Biberbach (DE); Andreas Schnapp, Biberbach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 51 days.

(21) Appl. No.: 10/025,426

(22) Filed: Dec. 19, 2001

(65) Prior Publication Data

US 2002/0123509 A1 Sep. 5, 2002

(30) Foreign Application Priority Data

Dec. 23, 2000 (DE) .......................................... 100 65 043

(51) Int. Cl.⁷ ...................... A61K 31/55; C07D 301/14; C07D 301/87
(52) U.S. Cl. .......................... 514/443; 549/31; 549/307; 514/469
(58) Field of Search ................................ 514/443, 469; 549/31, 307

(56) References Cited

U.S. PATENT DOCUMENTS 3,940,422 A * 2/1976 Harita et al. ................. 549/441
5,703,116 A 12/1997 Gaeta et al.

* cited by examiner

*Primary Examiner*—D. Margaret Seaman

(57) ABSTRACT

The present application relates to new carboxylic acid amides of general formula

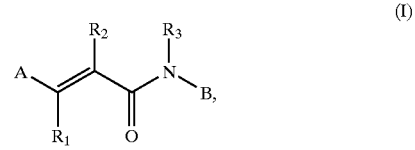

wherein
A, B and $R_1$ to $R_3$ are defined as in claim 1, processes for preparing them, pharmaceutical compositions containing these compounds and the use thereof and their preparation.

10 Claims, No Drawings

CARBOXYLIC ACID AMIDES, PHARMACEUTICAL COMPOSITIONS CONTAINING THESE COMPOUNDS, THEIR USE AND THE PREPARATION THEREOF

The last decade of oncological research has made it possible for the first time to achieve a molecular understanding of the regulatory mechanisms involved in the formation of tumours. These include, for example, the function of oncogenes, tumour suppressor genes, growth factors, receptors, signal transduction cascades, pro- and anti-apoptotic genes in controlling cell growth, differentiation, migration and cell death. These new findings have also shown, however, that cancer is a multifactorial disease at the molecular level, during the onset of which tissues may undergo malignant degeneration as a result of different mechanisms. This heterogeneity of the malignant cells in turn explains the clinical problems of tumour therapy.

As long ago as 1965 Hayflick postulated (Hayflick, Exp. Cell Res. 37, 614–636 (1965)) that the limited proliferative lifespan of normal somatic cells, replicative senescence, may act as a tumour suppressor mechanism. This hypothesis was supported by experimental work which showed that overcoming replicative senescence is a prerequisite for the malignant transformation of cells (Newbold et al. in Nature, 299, 633–636 (1989); Newbold and Overell in Nature, 304, 648–651 (1983)).

However, only in the last few years has there been any understanding of the molecular mechanisms by which somatic cells achieve the state of replicative senescence.

The ends of eukaryotic chromosomes, the telomers, consist of simple repetitive sequences the integrity of which is essential for the function and structure of the chromosomes. However, linear chromosomes lose a certain length of their telomers in each round of DNA replication, a phenomenon which was recognised by Watson back in 1972 (Watson in Nature New Biol. 239, 197–201 (1972)). The cumulative loss of telomeric DNA over numerous cell divisions constitutes the reason for the limited replicative potential of somatic cells, whereas more than 85% of all tumours in humans reactivate an enzyme, telomerase, to compensate for the loss of telomers and thus become immortal (see Shay and Bacchetti in European Journal of Cancer, 33, 787–791 (1997)).

Telomerase in humans is a ribonucleoprotein (RNP) which is made up of at least one catalytic subunit (hTERT), and one RNA (hTR). Both components have been molecularly cloned and characterised. Biochemically, telomerase is a reverse transcriptase which uses a sequence fragment in hTR as a matrix in order to synthesise a strand of telomeric DNA (Morin in Cell 59, 521–529 (1989)). Methods of identifying telomerase activity as well as methods of diagnosing and treating replicative senescence and immortality by modifying telomers and telomerase have already been described (Morin in Cell 59, 521–529 (1989); Kim et al. in Science 266, 2011–2014 (1994)).

Inhibitors of telomerase may be used for tumour therapy, as somatic cells, unlike tumour cells, are not dependent on telomerase.

Moreover, U.S. Pat. No. 3,940,422 inter alia describes the compound trans-3,4-dimethoxy-cinnamic acid-N-anthranilic acid-amide, which has antiallergenic properties, in particular.

It has now been found that the carboxylic acid amides of general formula

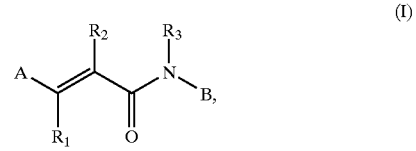

the isomers thereof, particularly the trans-isomers thereof, and the salts thereof, particularly the physiologically acceptable salts thereof, surprisingly have an inhibiting effect on telomerase.

The present invention relates to the new carboxylic acid amides of the above general formula I and the salts thereof, particularly the physiologically acceptable salts thereof, which have an inhibiting effect on telomerase, processes for preparing them, pharmaceutical compositions containing these compounds and the use thereof.

In the new carboxylic acid amides of the above general formula I $R_1$ denotes a hydrogen atom or a $C_{1-3}$-alkyl group,
$R_2$ denotes a hydrogen, fluorine, chlorine or bromine atom or a $C_{1-3}$-alkyl group,
$R_3$ denotes a hydrogen atom or a $C_{1-5}$-alkyl group,
A denotes a chromane or chromene group linked via a fused-on phenyl ring wherein a methylene group may be replaced by a carbonyl group,
or a bicyclic heteroaryl group consisting of
 a 5- or 6-membered heteroaryl group optionally substituted in the carbon skeleton by a fluorine, chlorine or bromine atom or by a $C_{1-3}$-alkyl or $C_{1-3}$-alkoxy group, wherein the 6-membered heteroaryl groups contain one, two or three nitrogen atoms and the 5-membered heteroaryl groups contain an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, and a phenyl ring fused to the abovementioned monocyclic heteroaryl groups via two adjacent carbon atoms, by means of which the bicyclic heteroaryl group is linked to the $R_1$-substituted alkene-carbon atom and which may also be substituted in the carbon skeleton by a fluorine, chlorine or bromine atom or by a $C_{1-3}$-alkyl or $C_{1-3}$-alkoxy group,
and B denotes a 5- or 6-membered heteroaryl group substituted by a carboxy group or by a group which may be converted into a carboxy group in vivo
or a phenyl or naphthyl group which is substituted in each case by a carboxy group, by a group which may be converted into a carboxy group in vivo or by a group which is negatively charged under physiological conditions, while the abovementioned phenyl group may additionally be substituted
 by a fluorine, chlorine, bromine or iodine atom,
 by a $C_{1-3}$-alkyl, trifluoromethyl, phenyl, hydroxy, $C_{1-3}$-alkoxy, $C_{1-3}$-alkyl-sulphonyloxy, phenylsulphonyloxy, carboxy, $C_{1-3}$-alkoxycarbonyl, formyl, $C_{1-3}$-alkylcarbonyl, $C_{1-3}$-alkylsulphonyl, phenylsulphonyl, nitro, pyrrolidino, piperidino, morpholino, N—($C_{1-3}$-alkyl)-piperazino, aminosulphonyl, $C_{1-3}$-alkylaminosulphonyl- or di-($C_{1-3}$-alkyl)-aminosulphonyl group,
 by an n-$C_{2-3}$-alkoxy group substituted in the 2 or 3 position by a di-($C_{1-3}$-alkyl)-amino group, by an amino group, by an N—($C_{1-3}$-alkyl)-amino or N,N-di-($C_{1-3}$-alkyl)-amino group wherein the alkyl moiety in the 2 or 3 position relative to the nitrogen atom may be substituted in each case by a $C_{1-3}$-alkoxy group, by an N-phenylamino, N-(phenyl-$C_{1-3}$-alkyl)-amino or N-(pyridyl-$C_{1-3}$-alkyl)-amino group, by an aminocarbonyl group which may be mono- or disubstituted at the amino-nitrogen atom by a $C_{1-3}$-alkyl group, by a pyrrolidinocarbonyl, piperidinocarbonyl, morpholinocarbonyl or N—($C_{1-3}$-alkyl)-piperazinocarbonyl group, by a sulphonyl group substituted by an amino, $C_{1-3}$-alkylamino, di-($C_{1-3}$-alkyl)-amino, pyrrolidino, piperidino, morpholino or N—($C_{1-3}$-alkyl)-piperazino group, by an amino or N—($C_{1-3}$-alkyl)-amino group which is substituted in each case at the amino-nitrogen atom by an aminocarbonyl, $C_{1-3}$-alkylaminocarbonyl, phenyl-$C_{1-3}$-alkylaminocarbonyl, phenylaminocarbonyl, pyridylaminocarbonyl, pyrrolidinocarbonyl, piperidinocarbonyl, morpholinocarbonyl or N—($C_{1-3}$-alkyl)-piperazinocarbonyl group, whilst in the abovementioned aminocarbonyl groups any hydrogen atom present may additionally be replaced by a $C_{1-3}$-alkyl group, or by a 5 or 6-membered heteroaryl group, whilst the abovementioned phenyl groups may additionally be substituted by another fluorine, chlorine or bromine atom or by another $C_{1-3}$-alkyl or $C_{1-3}$-alkoxy group and two $C_{1-3}$-alkoxy groups in the o position may be replaced by a methylenedioxy group, and the abovementioned 6-membered heteroaryl groups contain one, two or three nitrogen atoms and the abovementioned 5-membered heteroaryl groups contain an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, the isomers thereof and the salts thereof.

An essential feature of the invention is the fact that A denotes a bicyclic heteroaryl group which is linked via the phenyl ring to the $R_1$-substituted olefinic carbon atom.

By a group which can be converted in vivo into a carboxy group is meant, for example, a hydroxmethyl group, a carboxy group esterified with an alcohol, wherein the alcoholic moiety preferably denotes a $C_{1-6}$-alkanol, a phenyl-$C_{1-3}$-alkanol, a $C_{3-9}$-cycloalkanol, whilst a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol, a bicycloalkanol having a total of 8 to 10 carbon atoms which may additionally be substituted by one or two $C_{1-3}$-alkyl groups in the bicycloalkyl moiety, a 1,3-dihydro-3-oxo-1-isobenzfuranol or an alcohol of formula $R_a$—CO—O—($R_b CR_c$)—OH, wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom or a $C_{1-3}$-alkyl group, by a group which is negatively charged under physiological conditions is meant a carboxy, hydroxysulphonyl, phosphono, tetrazol-5-yl, phenylcarbonylaminocarbonyl, trifluoromethylcarbonylaminocarbonyl, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group.

Moreover, the saturated alkyl and alkoxy moieties containing more than 2 carbon atoms mentioned in the definitions given above and hereinafter also include the branched isomers thereof, such as the isopropyl, tert.butyl, isobutyl group, etc.

Preferred compounds of the above general formula I are those wherein $R_1$ denotes a hydrogen atom or a $C_{1-3}$-alkyl group, $R_2$ denotes a hydrogen, fluorine, chlorine or bromine atom or a $C_{1-3}$-alkyl group, $R_3$ denotes a hydrogen atom or a methyl group, A denotes a chromane or chromene group linked via a fused-on phenyl ring wherein a methylene group may be replaced by a carbonyl group, or a bicyclic heteroaryl group consisting of a 5 or 6-membered heteroaryl group optionally substituted in the carbon skeleton by a fluorine, chlorine or bromine atom, by a $C_{1-3}$-alkyl or $C_{1-3}$-alkoxy group, while the 6-membered heteroaryl groups contain one, two or three nitrogen atoms and the 5-membered heteroaryl groups contain an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, and a phenyl ring fused to the abovementioned monocyclic heteroaryl groups via two adjacent carbon atoms, by means of which the bicyclic heteroaryl group is linked to the $R_1$-substituted alkene-carbon atom and which may also be substituted in the carbon skeleton by a fluorine, chlorine or bromine atom or by a methyl or methoxy group, and B denotes a 5 or 6-membered heteroaryl group substituted by a carboxy group or by a group which may be converted into a carboxy group in vivo or a phenyl or naphthyl group which is substituted in each case by a carboxy group or by a group which may be converted into a carboxy group in vivo, while the abovementioned phenyl group is additionally substituted by a fluorine, chlorine or bromine atom, by a $C_{1-3}$-alkyl, trifluoromethyl, phenyl, hydroxy, $C_{1-3}$-alkoxy, carboxy, $C_{1-3}$-alkoxycarbonyl, formyl, $C_{1-3}$-alkylcarbonyl, $C_{1-3}$-alkylsulphonyl, phenylsulphonyl, nitro, pyrrolidino, piperidino, morpholino, N—($C_{1-3}$-alkyl)-piperazino, aminosulphonyl, $C_{1-3}$-alkylaminosulphonyl or di-($C_{1-3}$-alkyl)-aminosulphonyl group, by a n-$C_{2-3}$-alkoxy group substituted in the 2 or 3 position by a di-($C_{1-3}$-alkyl)-amino group, by an amino group, by an N—($C_{1-3}$-alkyl)-amino or N,N-di-($C_{1-3}$-alkyl)-amino group wherein the alkyl moiety in the 2 or 3 position relative to the nitrogen atom may be substituted in each case by a $C_{1-3}$-alkoxy group, by an N-phenylamino, N-(phenyl-$C_{1-3}$-alkyl)-amino or N-(pyridyl-$C_{1-3}$-alkyl)-amino group, by an aminocarbonyl group which may be mono or disubstituted at the amino-nitrogen atom by a $C_{1-3}$-alkyl group, by a pyrrolidinocarbonyl, piperidinocarbonyl, morpholinocarbonyl or N—($C_{1-3}$-alkyl)-piperazinocarbonyl group, by a sulphonyl group substituted by an amino, $C_{1-3}$-alkylamino, di-($C_{1-3}$-alkyl)-amino, pyrrolidino, piperidino, morpholino or N—($C_{1-3}$-alkyl)-piperazino group, or by an amino or N—($C_{1-3}$-alkyl)-amino group which is substituted in each case at the amino-nitrogen atom by an aminocarbonyl, $C_{1-3}$-alkylaminocarbonyl, phenyl-$C_{1-3}$-alkylaminocarbonyl, phenylaminocarbonyl, pyridylaminocarbonyl, pyrrolidinocarbonyl, piperidinocarbonyl, morpholinocarbonyl or N—($C_{1-3}$-alkyl)-piperazinocarbonyl group, wherein additionally any hydrogen atom present in one of the abovementioned aminocarbonyl groups may be replaced by a $C_{1-3}$-alkyl group, whilst the abovementioned phenyl groups may additionally be substituted by another fluorine, chlorine or bromine atom or by another $C_{1-3}$-alkyl or $C_{1-3}$-alkoxy group, and the abovementioned 6-membered heteroaryl groups contain one or two nitrogen atoms and the abovementioned 5-membered heteroaryl groups contain an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, the isomers thereof and the salts thereof.

Particularly preferred new compounds of the above general formula I are those wherein B and $R_1$ to $R_3$ are as hereinbefore defined, and A denotes a chromane or chromene group linked via a fused-on phenyl ring wherein a methylene group may be replaced by a carbonyl group, or a bicyclic heteroaryl group consisting of a 5 or 6-membered heteroaryl group optionally substituted in the carbon skeleton by a fluorine, chlorine or bromine atom, by a methyl or methoxy group, while the 6-membered heteroaryl groups contain one, two or three nitrogen atoms and the 5-membered heteroaryl groups contain an imino group optionally substituted by a methyl group, an oxygen or sulphur atom, or an imino group optionally substituted by a methyl group and an oxygen or sulphur atom or one or two nitrogen atoms, and a phenyl ring fused to the abovementioned monocyclic heteroaryl groups via two adjacent carbon atoms, by means of which the bicyclic heteroaryl group is linked to the $R_1$ substituted alkene-carbon atom and which may also be substituted in the carbon skeleton by a fluorine, chlorine or bromine atom or by a methyl or methoxy group, the isomers thereof and the salts thereof.

Most particularly preferred compounds of general formula I are those wherein $R_1$ denotes a hydrogen atom or a $C_{1-3}$-alkyl group,
$R_2$ denotes a hydrogen atom or a methyl group,
$R_3$ denotes a hydrogen atom,
A denotes a benzofuryl, benzothienyl, quinolyl or isoquinolyl group bound via the phenyl moiety to the $R_1$-substituted alkene-carbon atom and optionally substituted by a methyl group and B denotes a pyridyl, thienyl, pyrazolyl, quinolyl or isoquinolyl group substituted by a carboxy group or a phenyl group substituted by a carboxy, methoxycarbonyl or ethoxycarbonyl group, which may additionally be substituted by a fluorine, chlorine or bromine atom, by a methyl, trifluoromethyl, phenyl, hydroxymethyl, hydroxy, methoxy, 2-dimethylamino-ethoxy, nitro, methylsulphonylamino, phenylsulphonylamino, aminosulphonyl, pyrrolidino, piperidino or morpholino group, by an amino, N-methyl-amino or N-(2-methoxy-ethyl)-amino group which may be substituted in each case at the amino-nitrogen atom by a $C_{1-3}$-alkyl group, or by an aminocarbonyl, methylaminocarbonyl or dimethylaminocarbonyl group, whilst the abovementioned phenyl groups may additionally be substituted by another fluorine or chlorine atom or by another methyl or methoxy group, the isomers thereof and the salts thereof, particularly those compounds of general formula I wherein $R_1$ denotes a hydrogen atom, a methyl or ethyl group,
$R_2$ denotes a hydrogen atom,
$R_3$ denotes a hydrogen atom,
A denotes a benzothienyl, quinolyl or isoquinolyl group bound to the $R_1$-substituted alkene-carbon atom via the phenyl moiety and optionally substituted by a methyl group and B denotes a phenyl, thienyl or pyridinyl group substituted in each case by a carboxy group, while the abovementioned phenyl group may additionally be substituted by a fluorine, chlorine or bromine atom, by a methyl, hydroxy, $C_{1-3}$-alkoxy, pyrrolidino, piperidino, morpholino or N—($C_{1-3}$-alkyl)-piperazino group, by a 2-dimethylaminoethoxy group, by an amino, methylamino or dimethylamino group or by an aminocarbonyl, methylaminocarbonyl or dimethylaminocarbonyl group and the disubstituted phenyl groups may additionally be substituted by another fluorine atom or by another methyl or methoxy group, the isomers thereof and the salts thereof.

Most preferred are compounds of general formula I wherein $R_1$ denotes a methyl group,
$R_2$ denotes a hydrogen atom,
$R_3$ denotes a hydrogen atom,
A denotes a benzothienyl, quinolyl or isoquinolyl group bound to the $R_1$-substituted alkene-carbon atom via the phenyl moiety and B denotes a 2-carboxy-phenyl or 2-carboxy-thienyl group, while the abovementioned 2-carboxy-phenyl group may additionally be substituted in the phenyl nucleus by a fluorine, chlorine or bromine atom, by a methyl, hydroxy, $C_{1-3}$-alkoxy, amino, methylamino, dimethylamino or morpholino group, by a 2-dimethylaminoethoxy group or by an aminocarbonyl, methylaminocarbonyl or dimethylaminocarbonyl group and optionally additionally by another fluorine atom or by another methoxy group, the isomers thereof and the salts thereof.

The following are mentioned as examples of particularly preferred compounds:

(1) trans-3-(benzothien-6-yl)-but-2-enoic acid-N-(2-carboxy-phenyl)-amide,
(2) trans-3-(benzothien-5-yl)-but-2-enoic acid-N-(2-carboxy-phenyl)-amide,
(3) trans-3-(benzothien-6-yl)-but-2-enoic acid-N-(2-carboxy-4,5-dimethoxyphenyl)-amide,
(4) trans-3-(benzothien-6-yl)-but-2-enoic acid-N-(2-carboxy-6-methylphenyl)-amide,
(5) trans-3-(benzothien-6-yl)-but-2-enoic acid-N-(2-carboxy-4-fluorophenyl)-amide and
(6) trans-3-(quinolin-6-yl)-but-2-enoic acid-N-(2-carboxy-phenyl)-amide, as well as the salts thereof.

The carboxylic acid amides of the above general formula I are obtained, for example, by the following methods known per se:

a. Acylating an amine of general formula

(II)

wherein
$R_3$ and B are as hereinbefore defined, with a carboxylic acid of general formula

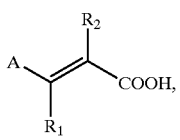

(III)

wherein
$R_1$, $R_2$ and A are as hereinbefore defined, or the reactive derivatives thereof.

The acylation is conveniently carried out with a corresponding halide or anhydride in a solvent such as methylene chloride, chloroform, carbon tetrachloride, ether, tetrahydrofuran, dioxane, benzene, chlorobenzene, toluene, acetonitrile or sulpholane, optionally in the presence of an inorganic or organic base such as triethylamine, N-ethyldiisopropylamine, N-methyl-morpholine or pyridine at temperatures between −20 and 200° C., but preferably at temperatures between −10 and 160° C.

However, the acylation may also be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, N,N'-carbonyldiimidazole or N,N'-thionyldiimidazole or triphenylphosphine/carbon tetrachloride, at temperatures between −20 and 200° C., but preferably at temperatures between −10 and 160° C.

b. In order to prepare a carboxylic acid amide of general formula I which contains a carboxy group:
converting a compound of general formula

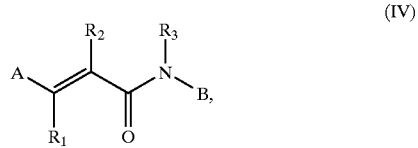

(IV)

wherein
$R_1$ to $R_3$, A and B are as hereinbefore defined, with the proviso that B contains a group which can be converted into a carboxy group, into a compound of general formula I which contains a carboxy group.

Examples of a group which can be converted into a carboxy group include carboxyl groups protected by protecting groups, such as the functional derivatives thereof, e.g. the unsubstituted or substituted amides, esters, thioesters, trimethylsilylesters, orthoesters or iminoesters thereof, which are conveniently converted into a carboxyl group by hydrolysis, the esters thereof with tertiary alcohols, e.g. the tert. butyl ester, which are conveniently converted into a carboxyl group by treating with an acid or by thermolysis, and the esters thereof with aralkanols, e.g. the benzyl ester, which are conveniently converted into a carboxyl group by hydrolysis.

The hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

The conversion of a tert. butyl or tert. butyloxycarbonyl group into a carboxy group can also be carried out by treating with an acid such as trifluoroacetic acid, formic acid, p-toluenesulphonic acid, sulphuric acid, hydrochloric acid, phosphoric acid or polyphosphoric acid optionally in an inert solvent such as methylene chloride, chloroform, benzene, toluene, diethylether, tetrahydrofuran or dioxane, preferably at temperatures between −10 and 120° C., e.g. at temperatures between 0 and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C.

The conversion of a benzyloxy or benzyloxycarbonyl group into a carboxy group may also be carried out hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at ambient temperature, and at a hydrogen pressure of 1 to 5 bar.

If according to the invention a compound of general formula I is obtained which contains a hydroxy group, this may be converted into a corresponding sulphonyloxy compound by means of a sulphonyl halide, or if a compound of general formula I is obtained which contains a cyano group, this can be converted by means of hydrazoic acid into a corresponding tetrazolyl compound, or if a compound of general formula I is obtained which contains an amino or imino group with a basic hydrogen atom, this can be converted by acylation or sulphonylation into a correspondingly acylated compound or into a corresponding prodrug compound, or if a compound of general formula I is obtained which contains a carboxy group, this can be converted into a compound which contains a group which may be converted into a carboxy group in vivo, or if a compound of general formula I is obtained which contains one or two carboxy groups, this can be converted by reduction with a complex metal hydride into a compound which contains one or two hydroxymethyl groups.

The subsequent sulphonylation is conveniently carried out with a corresponding halide in a solvent such as methylene chloride, chloroform, carbon tetrachloride, ether, tetrahydrofuran, dioxane, benzene, toluene, acetonitrile or sulpholane, optionally in the presence of an inorganic or organic base such as triethylamine, N-ethyl-diisopropylamine, N-methyl-morpholine or pyridine at temperatures between −20 and 200° C., but preferably at temperatures between −10 and 160° C.

The subsequent preparation of a compound of general formula I which contains a tetrazole group is preferably carried out in a solvent such as benzene, toluene or dimethylformamide at temperatures between 80 and 150° C., preferably between 120 and 130° C. The hydrazoic acid required is conveniently liberated during the reaction from an alkali metal azide, e.g. from sodium azide, in the presence of a weak acid such as ammonium chloride. The reaction may also be carried out with another salt or derivative of hydrazoic acid, preferably with aluminium azide or tributyl tin azide, and the tetrazole compound optionally obtained in this way is then liberated from the salt contained in the reaction mixture by acidification with a dilute acid such as 2N hydrochloric acid or 2N sulphuric acid.

The subsequent acylation or sulphonylation or the subsequent conversion into a corresponding prodrug compound is preferably carried out with a corresponding acid halide in a solvent such as methylene chloride, chloroform, carbon tetrachloride, ether, tetrahydrofuran, dioxane, benzene, toluene, acetonitrile or sulpholane, optionally in the presence of an inorganic or organic base such as triethylamine, N-ethyl-diisopropylamine, N-methyl-morpholine or pyridine at temperatures between −20 and 200° C., but preferably at temperatures between −10 and 160° C.

The subsequent conversion of a carboxy group into a group which may be converted into a carboxy group in vivo is preferably carried out by esterification with a corresponding alcohol or by alkylation of the carboxy group. The esterification is conveniently carried out in a solvent or mixture of solvents such as methylene chloride, benzene, toluene, chlorobenzene, tetrahydrofuran, benzene/tetrahydrofuran or dioxane, but preferably in an excess of the alcohol used in the presence of a dehydrating agent, e.g. in the presence of hydrochloric acid, sulphuric acid, isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, 2-(1H-benzotriazol-1-yl)-1,1,3,3-tetramethyluronium-tetrafluoroborate, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyl-diisopropylamine or N,N-dimethylamino-pyridine, conveniently at temperatures between 0 and 150° C., preferably at temperatures between 0 and 80° C., and the alkylation is conveniently carried out with a corresponding halide in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously serve as solvent, or optionally in the presence of silver carbonate or silver oxide at temperatures between −30 and 100° C., but preferably at temperatures between −10 and 80° C.

The subsequent reduction is preferably carried out in the presence of a complex metal hydride such as lithium aluminium hydride or lithium triethyl borohydride in a solvent such as tetrahydrofuran, conveniently at the boiling temperature of the solvent used.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, protecting groups for a carboxy group may be a trimethylsilyl, methyl, ethyl, tert.butyl, benzyl or tetrahydropyranyl group and protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

The compounds of general formulae 11 to IV used as starting materials are known from the literature in some cases but may also be prepared by methods known from the literature (cf. for example Fulton et al. in J. Chem. Soc. 1939, page 200, S. Sano et al. in Chem. Commun. 6, page 539 (1997) and D. H. Klaubert et al. in J. Med. Chem. 24, 742–748 (1981)).

Moreover, the compounds of general formula I obtained may be resolved into their enantiomers and/or diastereomers, as mentioned hereinbefore. Thus, for example, compounds with at least one optically active carbon atom may be separated into their enantiomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 stereogenic centres may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain an acidic group such as a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, lysine, cyclohexylamine, ethanolamine, diethanolamine and triethanolamine.

As already mentioned hereinbefore, the carboxylic acid amides of general formula I and the salts thereof, particularly the physiologically acceptable salts thereof, have an inhibiting effect on telomerase.

The inhibiting effect of the carboxylic acid amides of general formula I on telomerase was investigated as follows:
Materials and Methods:
1.Preparation of nuclear extracts from HeLa cells: Nuclear extracts were prepared according to Dignam (Dignam et al. in Nucleic Acids Res. 11, 1475–1489 (1983)). All the steps were carried out at 4° C., all the equipment and solutions were pre-cooled to 4° C. At least $1 \times 10^9$ HeLa-S3 cells growing in suspension culture (ATCC catalogue number CCL-2.2) were harvested by centrifuging for 5 minutes at 1000× g and washed once with PBS buffer (140 mM KCl; 2.7 mM KCl; 8.1 mM $Na_2HPO_4$; 1.5 mM $KH_2PO_4$). After the cell volume had been determined, the cells were suspended in 5 times the volume of hypotonic buffer (10 mM HEPES/KOH, pH 7.8; 10 mM KCl; 1.5 mM $MgCl_2$) and then left for 10 minutes at 4° C. After centrifuging for 5 minutes at 1000× g the cell pellet was suspended in twice the volume of hypotonic buffer in the presence of 1 mM DTE and 1 mM PMSF and broken up with a Dounce homogeniser. The homogenised material was made isotonic with 0.1 volume of 10-fold saline buffer (300 mM HEPES/KOH, pH 7.8; 1.4 M KCl; 30 mM $MgCl_2$). The cell nuclei were separated from the cytoplasmic components by centrifuging and then suspended in twice the volume of nuclear extraction buffer (20 mM HEPES/KOH, pH 7.9; 420 mM KCl; 1.5 mM $MgCl_2$; 0.2 mM EDTA; 0.5 mM DTE; 25% glycerol). The nuclei were broken up using a Dounce homogeniser and incubated for 30 minutes at 4° C. with gentle stirring. Any insoluble ingredients were removed by centrifuging for 30 minutes at 10,000 rpm (SS-34 Rotor). Then the nuclear extract was dialysed for 4–5 hours against AM-100 buffer (20 mM tris/HCl, pH 7.9; 100 mM KCl; 0.1 mM EDTA; 0.5 mM DTE; 20% glycerol). The nuclear extracts obtained were frozen in liquid nitrogen and stored at −80° C.

2. Telomerase test: The activity of telomerase in nuclear extracts from HeLa cells was determined using the method described by Morin (Morin in Cell 59, 521–529 (1989)). The nuclear extract (up to 20 μl per reaction) was incubated for 120 minutes at 30° C. in a volume of 40 μl in the presence of 25 mM Tris/HCl pH 8.2, 1.25 mM dATP, 1.25 mM TTP, 6.35 μM dGTP; 15 μCi α-$^{32}$P-dGTP (3000 Ci/Mmol), 1 mM $MgCl_2$, 1 mM EGTA, 1.25 mM spermidine, 0.25 U RNasin, and 2.5 μM of an oligonucleotide primer (for example TEA-fw [CAT ACT GGC GAG CAG AGT T], or TTA GGG TTA GGG TTA GGG) (=telomerase reaction). If the inhibition constant of potential telomerase inhibitors was to be determined, these were also added to the telomerase reaction in a concentration range of from 1 nM to 100 μM.

The reaction was then stopped by the addition of 50 μl of RNase stop buffer (10 mM tris/HCL, pH 8.0; 20 mM EDTA; 0.1 mg/ml of RNase A 100 U/ml of RNase T1; 1000 cpm of an α-$^{32}$P-dGTP labelled, 430 bp DNA fragment) and incubation was continued for a further 15 minutes at 37° C. Proteins present in the reaction mixture were cleaved by the addition of 50 μl of proteinase K buffer (10 mM tris/HCL, pH 8.0; 0.5% SDS; 0.3 mg/ml of proteinase K) and subsequent incubation for 15 min at 37° C. The DNA was purified by extracting twice with phenol-chloroform and precipitated by adding 2.4 M ammonium acetate; 3 μg tRNA and 750 μl ethanol. Then the precipitated DNA was washed with 500 μl of 70% ethanol, dried at ambient temperature, taken up in 4 μl of formamide probe buffer (80% (v/v) formamide; 50 mM of tris-borate, pH 8.3; 1 mM EDTA; 0.1 (w/v) of xylene cyanol; 0.1% (w/v) bromophenol blue) and separated by electrophoresis on a sequence gel (8% polyacrylamide, 7 M urea, 1× TBE buffer). The DNA synthesised by telomerase in the presence or absence of potential inhibitors was identified and quantified by Phospho-Imager Analysis (Molecular Dynamics) and in this way the concentration of inhibitor which inhibits the telomerase activity by 50% ($IC_{50}$) was determined. The radiolabelled DNA fragment to which the RNase stop buffer had been added was used as an internal control for the yield.

The inhibitors of Examples 1 to 6 inhibited the telomerase activity by more than 50% at a concentration of 5 μM.

The following abbreviations were used in the foregoing description:

| | |
|---|---|
| bp | base pairs |
| DNA | deoxyribonucleic acid |
| DTE | 1,4-dithioerythritol |
| dATP | deoxyadenosine triphosphate |
| dGTP | deoxyguanosine triphosphate |
| EDTA | ethylenediamine-tetraacetic acid |
| EGTA | ethyleneglycol-bis-(2-aminoethyl)-tetraacetic acid |
| HEPES | 4-(2-hydroxyethyl)-piperazine-1-ethanesulphonic acid |
| PMSF | phenylmethanesulphonylfluoride |
| RNase | ribonuclease |
| RNasin ® | ribonuclease inhibitor (Promega GmbH, Mannheim) |
| tRNA | transfer ribonucleic acid |
| TTP | thymidine triphosphate |
| TRIS | tris-(hydroxymethyl)-aminomethane |
| TBE | TRIS-borate-EDTA |
| rpm | revolutions per minute |

In view of their biological properties, the carboxylic acid amides of general formula I are suitable for treating pathophysiological processes which are characterised by an increased telomerase activity. These are e.g. tumour diseases such as carcinomas, sarcomas and leukaemias including skin cancer (e.g. plate epithelial carcinoma, basalioma, melanoma), small-cell bronchial carcinoma, non-small-cell bronchial carcinoma, salivary gland carcinoma, oesophageal carcinoma, laryngeal carcinoma, pharyngeal carcinoma, thyroid carcinoma, gastric carcinoma, colorectal carcinoma, pancreatic carcinoma, carcinoma of the liver, carcinoma of the breast, uterine carcinoma, vaginal carcinoma, ovarian carcinoma, prostate carcinoma, testicular carcinoma, bladder carcinoma, renal carcinoma, Wilms' tumour, retinoblastoma, astrocytoma, oligodendroglioma, meningioma, neuroblastoma, myeloma, medulloblastoma, neurofibrosarcoma, thymoma, osteosarcoma, chondrosarcoma, Ewing's sarcoma, fibrosarcoma, histiocytoma, dermatofibrosarcoma, synovialoma, leiomyosarcoma, rhabdomyosarcoma, liposarcoma, Hodgkin's lymphoma, non-Hodgkin's lymphoma, chronic myeloid leukaemia, chronic lymphatic leukaemia, acute promyelocytic leukaemia, acute lymphoblastoid leukaemia and acute myeloid leukaemia.

In addition, the compounds may also be used to treat other diseases which have an increased rate of cell division or increased telomerase activity, such as e.g. epidermal hyperproliferation (psoriasis), inflammatory processes (rheumatoid arthritis), diseases of the immune system, etc.

The compounds are also useful for treating parasitic diseases in man and animals, such as e.g. worm or fungal diseases as well as diseases caused by protozoan pathogens, such as e.g. Zooflagellata (Trypanosoma, Leishmania, Giardia), Rhizopoda (Entamoeba spp.), Sporozoa (Plasmodium spp., Toxoplasma spp.), Ciliata, etc.

For this purpose the carboxylic acid amides of general formula I may optionally be used in conjunction with other pharmacologically active compounds and therapeutic preparations which will reduce tumour size, and incorporated in conventional galenic preparations. These may be used, for example, in tumour therapy, in monotherapy or in conjunction with irradiation, surgical interventions or other anti-tumour therapeutics, e.g. in conjunction with topoisomerase inhibitors (e.g. etoposide), mitosis inhibitors (e.g. paclitaxel, vinblastine), cell cycle inhibitors (e.g. flavopyridol), inhibitors of signal transduction (e.g. farnesyltransferase inhibitors), compounds which interact with nucleic acid (e.g. cis-platin, cyclophosphamide, adriamycin), hormone antagonists (e.g. tamoxifen), inhibitors of metabolic processes (e.g. 5-FU etc.), cytokines (e.g. interferons), tumour vaccines, antibodies, etc. These combinations may be given either simultaneously or sequentially.

The daily dose is 0.1 to 3 g by oral or intravenous route, divided up into one to four doses a day. For this purpose the compounds of general formula I, optionally in conjunction with the other active substances mentioned above, may be formulated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof to produce conventional galenic preparations such as plain or coated tablets, capsules, powders, suspensions or suppositories.

The following Examples are intended to illustrate the invention in more detail:

EXAMPLE 1 trans-3-(benzothien-6-yl)-but-2-enoic acid-N-(2-carboxyphenyl)-amide 1a) ethyl trans-3-(benzothien-6-yl)-but-2-enoate 3.81 g (17.0 mmol) of diethyl ethoxycarbonylmethane phosphonate were combined with 1.91 g (17.0 mmol) of potassium tert. butoxide in 60 ml dimethylformamide and stirred for 20 minutes at ambient temperature. Then 3.00 g (17 mmol) of (benzothien-6-yl)-ethanone (for synthesis see S. L. Graham et al., J. Med. Chem. 32 (12), p.2548–54 (1989)) were added and stirring was continued for another 17 hours at ambient temperature. The reaction mixture was then stirred into about 100 ml of ice water, about 5 g of sodium chloride were added and the mixture was extracted three times with 40 ml ethyl acetate. Chromatographic purification of the crude product thus obtained using 200 g of silica gel (petroleum ether +5% ethyl acetate) yielded 3.01 g (71% of theory) of ethyl trans-3-(benzothien-6-yl)-but-2-enoate.

$C_{14}H_{14}O_2S$ (246.3)

$R_f$ value: 0.55 (silica gel, petroleum ether/ethyl acetate 4:1)

1b) trans-3-(benzothien-6-yl)-but-2-enoic acid 3.00 g (12.2 mmol) of ethyl trans-3-(benzothien-6-yl)-but-2-enoate were stirred in 70 ml of ethanol and 25 ml of 2N sodium hydroxide solution for two hours at 50° C. The alcohol was then evaporated off in vacuo and the solution was acidified with hydrochloric acid. The crude product thus precipitated was chromatographed over 200 g of silica gel (dichloromethane+1–4% ethanol).

$C_{12}H_{10}O_2S$ (218.3)

Yield: 2.03 g (75% of theory)

$R_f$ value: 0.22 (silica gel, dichloromethane/ethanol 50:1)

1c) trans-3-(benzothien-6-yl)-but-2-enoic acid-N-(2-methoxycarbonyl-phenyl)-amide 420 mg (1.92 mmol) of trans-3-(benzothien-6-yl)-but-2-enoic acid were stirred in 2 ml of thionyl chloride after the addition of 0.01 ml of dimethylformamide for 30 minutes at ambient temperature and then evaporated to dryness in vacuo. The acid chloride thus obtained was refluxed in crude form together with 287 mg (1.90 mmol) of methyl anthranilate in 30 ml of toluene for four hours. The mixture was then evaporated to dryness in vacuo and the residue was chromatographed over 100 g of silica gel (petroleum ether/ethyl acetate 7:3).

$C_{20}H_{17}NO_3S$ (351.4)

Yield: 480 mg (71% of theory)

$R_f$ value: 0.62 (silica gel, petroleum ether/ethyl acetate 4:1)

Mass spectrum: $(M+Na)^+=374$ $(M-H)^-=350$ 1d) trans-3-(benzothien-6-yl)-but-2-enoic acid-N-(2-carboxyphenyl)-amide 480 mg (1.37 mmol) of trans-3-(benzothien-6-yl)-but-2-enoic acid-N-(2-methoxycarbonyl-phenyl)-amide were stirred in 30 ml of methanol and 2 ml of 2N sodium hydroxide solution for two hours at ambient temperature, then the alcohol was evaporated off in vacuo, the residue was diluted with about 30 ml of water and acidified with hydrochloric acid. The product precipitated was suction filtered, washed with water and dried.

$C_{19}H_{15}NO_3S$ (337.4)

Yield: 400.0 mg (87% of theory)

$R_f$ value: 0.22 (silica gel, dichloromethane/ethanol 50:1)

Mass spectrum: $(M+Na)^+=360$ $(M-H)^-=336$ $(M+2Na—H)^+=382$

EXAMPLE 2 trans-3-(benzothien-5-yl)-but-2-enoic acid-N-(2-carboxyphenyl)-amide 2a) ethyl trans-3-(benzothien-5-yl)-but-2-enoate Prepared analogously to Example 1 a from (benzothien-5-yl)-ethanone (for synthesis see S. Datta et al., J. Chem. Soc. Perkin Trans. 1, 1989, p. 603–7).

$C_{14}H_{14}O_2S$ (246.3)

Yield: 2.70 g (41% of theory)

$R_f$ value: 0.72 (silica gel, petroleum ether/ethyl acetate 4:1)

Mass spectrum: $(M+Na)^+=269$ 2b) trans-3-(benzothien-5-yl)-but-2-enoic acid

Prepared analogously to Example 1 b from trans-3-(benzothien-5-yl)-but-2-enoate ethyl and methanolic sodium hydroxide solution.

$C_{12}H_{10}O_2S$ (218.3)

Yield: 2.20 g (92% of theory)

$R_f$ value: 0.48 (silica gel, dichloromethane/ethanol 9:1)

2c) trans-3-(benzothien-5-yl)-but-2-enoic acid-N-(2-methoxycarbonyl-phenyl)-amide Prepared analogously to Example 1c from 1.08 g (4.56 mmol) of trans-3-(benzothien-5-yl)-but-2-enoic acid and methyl anthranilate.

$C_{20}H_{17}NO_3S$ (351.4)

Yield: 1.10 g (69% of theory)

$R_f$ value: 0.62 (silica gel, petroleum ether/ethyl acetate 4:1)

Mass spectrum: $(M+Na)^+=374$ $(M+H)^+=352$ $(M-H)^-=350$ 2d) trans-3-(benzothien-5-yl)-but-2-enoic acid-N-(2-carboxyphenyl)-amide Prepared analogously to Example 1d from 1.10 g (3.13 mmol) of trans-3-(benzothien-5-yl)-but-2-enoic acid-N-(2-methoxycarbonyl-phenyl)-amide and methanolic sodium hydroxide solution.

$C_{19}H_{15}NO_3S$ (337.4)

Yield: 350 mg (33% of theory)

$R_f$ value: 0.30 (silica gel, dichloromethane/ethanol 19:1)

Mass spectrum: $(M+Na)^+=360$ $(M-H)^-=336$ $(M+2Na-H)^+=382$

EXAMPLE 3 trans-3-(benzothien-6-yl)-but-2-enoic acid-N-(2-carboxy-4,5-dimethoxy-phenyl)-amide Prepared analogously to Example 1 from trans-3-(benzothien-6-yl)-but-2-enoic acid-N-(4,5-dimethoxy-2-methoxycarbony-phenyl)-amide and methanolic sodium hydroxide solution.

$C_{21}H_{19}NO_5S$ (397.5)

Yield: 79% of theory $R_f$ value: 0.39 (silica gel, dichloromethane/ethanol 19:1)

Mass spectrum: $(M+Na)^+=420$ $(M-H)^-=396$ $(M+2Na-H)^+=442$

EXAMPLE 4 trans-3-(benzothien-6-yl)-but-2-enoic acid-N-(2-carboxy-6-methyl-phenyl)-amide

Prepared analogously to Example 1 from trans-3-(benzothien-6-yl)-but-2-enoic acid-N-(6-methyl-2-methoxycarbony-phenyl)-amide and methanolic sodium hydroxide solution.

$C_{20}H_{17}NO_3S$ (351.4)

Yield: 47% of theory $R_f$ value: 0.28 (silica gel, dichloromethane/ethanol 19:1)

Mass spectrum: $(M+Na)^+=374$ $(M-H)^-=350$ $(M+2Na-H)^+=396$

EXAMPLE 5 trans-3-(benzothien-6-yl)-but-2-enoic acid-N-(2-carboxy-4-fluorophenyl)-amide

Prepared analogously to Example 1 from trans-3-(benzothien-6-yl)-but-2-enoic acid-N-(4-fluoro-2-methoxycarbony-phenyl)-amide and methanolic sodium hydroxide solution.

$C_{19}H_4FNO_3S$ (355.4)

Yield: 62% of theory $R_f$ value: 0.26 (silica gel, dichloromethane/ethanol 19:1)

Mass spectrum: $(M-H)^-=354$ $(M+2Na-H)^+=400$

EXAMPLE 6 trans-3-(quinolin-6-yl)-but-2-enoic acid-N-(2-carboxyphenyl)-amide 6a) ethyl trans-3-(quinolin-6-yl)-but-2-enoate Prepared analogously to Example 1a from 1.71 g (10.0 mmol) of (quinolin-6-yl)-ethanone (for synthesis see: Lugowkin, Zh. Obshch. Khim. 25 English edition p.371 (1955)).

$C_{15}H_{15}NO_2$ (241.3)

Yield: 1.80 g (75% of theory)

$R_f$ value: 0.41 (silica gel, petroleum ether/ethyl acetate 2:1)

Mass spectrum: $(M+Na)^+=264$ 6b) trans-3-(quinolin-6-yl)-but-2-enoic acid Prepared analogously to Example 1 b from 1.80 g (7.46 mmol) of ethyl trans-3-(quinolin-6-yl)-but-2-enoate and methanolic sodium hydroxide solution.

$C_{13}H_{11}NO_2$ (213.2)

Yield: 0.80 g (50% of theory)

$R_f$ value: 0.21 (silica gel, dichloromethane/ethanol 19:1)

Mass spectrum: $(M+H)^+=214$ $(M-H)^-=212$ 6c) trans-3-(quinolin-6-yl)-but-2-enoic acid-N-(2-methoxycarbonyl-Phenyl)-amide Prepared analogously to Example 1c from 0.27 g (1.17 mmol) of trans-3-(quinolin-6-yl)-but-2-enoic acid and methyl anthranilate.

$C_{21}H_{18}N_2O_3$ (346.4)

Yield: 0.34 g (84% of theory)

$R_f$ value: 0.54 (silica gel, petroleum ether/ethyl acetate 4:1)

Mass spectrum: $(M+Na)^+=369$ $(M+H)^+=347$ $(M-H)^-=345$ 6d) trans-3-(quinolin-6-yl)-but-2-enoic acid-N-(2-carboxyphenyl)-amide Prepared analogously to Example 1d from 340 mg (0.98 mmol) of trans-3-(quinolin-6-yl)-but-2-enoic acid-N-(2- methoxycarbonyl-phenyl)-amide and methanolic sodium hydroxide solution.

$C_{20}H_{16}N_2O_3$ (332.4)

Yield: 300 mg (92% of theory)

$R_f$ value: 0.27 (silica gel, dichloromethane/ethanol 19:1)

Mass spectrum: $(M+2Na-H)^+=377$ $(M-H)^-=331$

EXAMPLE 7
Tablets Containing 50 mg of Active Substance

| | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

The active substance, $CaHPO_4$, lactose and corn starch are evenly moistened with an aqueous PVP solution. The mass is passed through a 2-mm screen, dried in a circulating air drier at 50° C. and screened again.

After the lubricant has been mixed in, the granules are compressed in a tablet-making machine.

EXAMPLE 8
Coated Tablets Containing 50 mg of Active Substance

| | |
|---|---|
| Active substance | 50.0 mg |
| Lysine | 25.0 mg |
| Lactose | 60.0 mg |
| Corn starch | 34.0 mg |
| Gelatine | 10.0 mg |
| Magnesium stearate | 1.0 mg |
| | 180.0 mg |

Preparation:

The active substance is mixed with the excipients and moistened with an aqueous gelatine solution. After screening and drying, the granules are mixed with magnesium stearate and compressed to form tablet cores.

The cores thus produced are covered with a coating by known methods. The coating suspension or solution may have colouring added to it.

EXAMPLE 9
Coated Tablets Containing 100 mg of Active Substance

| | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation:

The active substance is mixed with the excipients and moistened with an aqueous PVP solution. The moist mass is passed through a 1.5 mm screen and dried at 45° C. After drying, the mass is screened again and the magnesium stearate is added. This mixture is compressed to form tablet cores.

The cores thus produced are covered with a coating by known methods. The coating suspension or solution may have colouring added to it.

EXAMPLE 10
Capsules Containing 250 mg of Active Substance

| | |
|---|---|
| Active substance | 250.0 mg |
| Corn starch | 68.5 mg |
| Magnesium stearate | 1.5 mg |
| | 320.0 mg |

Preparation:

Active substance and corn starch are mixed together and moistened with water. The moist mass is screened and dried. The dry granules are screened and mixed with magnesium stearate. The final mixture is packed into size 1 hard gelatine capsules.

What is claimed is:

1. A carboxylic acid amide of formula I

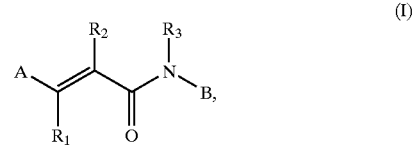

wherein $R_1$ is a hydrogen atom or a $C_{1-3}$-alkyl group, $R_2$ is a hydrogen, fluorine, chlorine or bromine atom or a $C_{1-3}$-alkyl group, $R_3$ is a hydrogen atom or a $C_{1-5}$-alkyl group, A is a bicyclic heteroaryl group consisting of
   a 5-membered heteroaryl group optionally substituted in the carbon skeleton by a fluorine, chlorine or bromine atom or by a $C_{1-3}$-alkyl or $C_{1-3}$-alkoxy group, wherein the 5-membered heteroaryl group contains an oxygen or sulphur atom, and
   a phenyl ring fused to the abovementioned monocyclic heteroaryl groups via two adjacent carbon atoms, by means of which the bicyclic heteroaryl group is linked to the $R_1$-substituted alkene-carbon atom and which may also be substituted in the carbon skeleton by a fluorine, chlorine or bromine atom or by a $C_{1-3}$-alkyl or $C_{1-3}$-alkoxy group, and B is a phenyl or naphthyl group which is substituted in each case by a carboxy group, by a group which may be converted into a carboxy group in viva or by a group which is negatively charged under physiological conditions, while the abovementioned phenyl group may additionally be substituted
   by a fluorine, chlorine, bromine or iodine atom,
   by a $C_{1-3}$-alkyl, trifluoromethyl, phenyl, hydroxy, $C_{1-3}$-alkyl-sulphonyloxy, phenylsulphonyloxy, carboxy, $C_{1-3}$-alkoxycarbonyl, formyl, $C_{1-3}$-alkylcarbonyl, $C_{1-3}$-alkylsulphonyl, phenylsulphonyl nitro, pyrrolidino, piperidino, morpholino, N—($C_{1-3}$-alkyl)-piperazino, aminosulphonyl, $C_{1-3}$-alkylaminosulphonyl- or di-($C_{1-3}$-aminosulphonyl group,
   by an n-$C_{2-3}$-alkoxy group substituted in the 2 or 3 position by a di-($C_{1-3}$-alkyl)-amino group,
   by an amino group, by an N—($C_{1-3}$-alkyl)-amino or N,N-di-($C_{1-3}$-alkyl)-amino group wherein the alkyl moiety in the 2 or 3 position relative to the nitrogen atom may be substituted in each case by a $C_{1-3}$-alkoxy group, by an N-phenylamino, N-(phenyl-$C_{1-3}$-alkyl)-amino or N-(pyridyl-$C_{1-3}$-alkyl)-amino group, by an aminocarbonyl group which may be mono- or disubstituted at the amino-nitrogen atom be a $C_{1-3}$-alkyl group, by a pyrrolidinocarbonyl piperidinocarbonyl morpholinocarbonyl or N—($C_{1-3}$-alkyl)-piperazinocarbonyl group, by a sulphonyl group substituted by an amino, $C_{1-3}$-alkylamino, di-($C_{1-3}$-alkyl)-amino, pyrrolidino, piperidino, morpholino or N—($C_{1-3}$-alkyl)-piperazino group, by an amino or N—($C_{1-3}$-alkyl)-amino group which is substituted in each case at the amino-nitrogen atom by an aminocarbonyl, $C_{1-3}$-alkylaminocarbonyl, phenyl-$C_{1-3}$-alkylaminocarbonyl, phenylaminocarbonyl, pyridylaminocarbonyl, pyrrolidinocarbonyl, piperidinocarbonyl, morpholinocarbonyl or N—($C_{1-3}$-alkyl)-piperazinocarbonyl group, whilst in the abovementioned aminocarbonyl groups any hydrogen atom present may additionally be replaced by a $C_{1-3}$-alkyl group, or by a 5- or 6-membered heteroaryl group, whilst the abovementioned phenyl groups may additionally be substituted by another fluorine, chlorine or bromine atom or by another $C_{1-3}$-alkyl or $C_{1-3}$-alkoxy group and two $C_{1-3}$-alkoxy groups in the o position may be replaced by a methylenedioxy group, and the abovementioned 6-membered heteroaryl groups contain one, two or three nitrogen atoms and, unless stated otherwise, the abovementioned 5-membered heteroaryl groups contain an imino group optionally substituted by a $C_{1-3}$-alkyl group, an oxygen or sulphur atom, or an imino group optionally substituted by a $C_{1-3}$-alkyl group and an oxygen or sulphur atom or one or two nitrogen atoms, an isomer thereof or a salt thereof.

2. The carboxylic acid amide according to claim 1, wherein $R_1$ is a hydrogen atom or a $C_{1-3}$-alkyl group, $R_2$ is a hydrogen, fluorine, chlorine or bromine atom or a $C_{1-3}$-alkyl group, $R_3$ is a hydrogen atom or a methyl group, A is a bicyclic heteroaryl group consisting of
a 5-membered heteroaryl group optionally substituted in the carbon skeleton by a fluorine, chlorine or bromine atom, by a $C_{1-3}$-alkyl or $C_{1-3}$-alkoxy group, while the 5-membered heteroaryl group contains an oxygen or sulphur atom, and
a phenyl ring fused to the abovementioned monocyclic heteroaryl group via two adjacent carbon atoms, by means of which the bicyclic heteroaryl group is linked to the $R_1$-substituted alkene-carbon atom and which may also be substituted in the carbon skeleton by a fluorine, chlorine or bromine atom or by a methyl or methoxy group, and B is a phenyl or naphthyl group which is substituted in each case by a carboxy group or by a group which may be converted into a carboxy group in viva, while the abovementioned phenyl group is additionally substituted by a fluorine, chlorine or bromine atom, by a $C_{1-3}$-alkyl, trifluoromethyl, phenyl, hydroxy, $C_{1-3}$-alkoxy, carboxy, $C_{1-3}$-alkoxycarbonyl, formyl, $C_{1-3}$-alkylcarbonyl, $C_{1-3}$-alkylsulphonyl, phenylsulphonyl, nitro, pyrrolidino, piperidino, morpholino, N—($C_{1-3}$-alkyl)-piperazino, aminosulphonyl, $C_{1-3}$-alkylaminosulphonyl or di-($C_{1-3}$-alkyl)-aminosulphonyl group, by a N—$C_{2-3}$-alkoxy group substituted in the 2 or 3 position by a di-($C_{1-3}$-alkyl)-amino group, by an amino group, by an N—($C_{1-3}$-alkyl)-amino or N,N-di-($C_{1-3}$-alkyl)-amino group wherein the alkyl moiety in the 2 or 3 position relative to the nitrogen atom may be substituted in each case by a $C_{1-3}$-alkoxy group, by an N-phenylamino, N-(phenyl-$C_{1-3}$-alkyl)-amino or N-(pyridyl-$C_{1-3}$-alkyl)-amino group, by an aminocarbonyl group which may be mono or disubstituted at the amino-nitrogen atom by a $C_{1-3}$-alkyl group, by a pyrrolidinocarbonyl, piperidinocarbonyl, morpholinocarbonyl or N—($C_{1-3}$-alkyl)-piperazinocarbonyl group, by a sulphonyl group substituted by an amino, $C_{1-3}$-alkylamino, di-($C_{1-3}$-alkyl)-amino, pyrrolidino, piperidino, morpholino or N—($C_{1-3}$-alkyl)-piperazino group, or by an amino or N—($C_{1-3}$-alkyl)-amino group which is substituted in each case at the amino-nitrogen atom by an aminocarbonyl, $C_{1-3}$-alkylaminocarbonyl, phenyl-$C_{1-3}$-alkylaminocarbonyl, phenylaminocarbonyl, pyridylaminocarbonyl, pyrrolidinocarbonyl, piperidinocarbonyl, morpholinocarbonyl or N—($C_{1-3}$-alkyl)-piperazinocarbonyl group, wherein additionally any hydrogen atom present in one of the abovementioned aminocarbonyl groups may be replaced by a $C_{1-3}$-alkyl group, whilst the abovementioned phenyl groups may additionally be substituted by another fluorine, chlorine or bromine atom or by another $C_{1-3}$-alkyl or $C_{1-3}$-alkoxy group, an isomer thereof or a salt thereof.

3. The carboxylic acid amide according to claim 2, wherein

A is a bicyclic heteroaryl group consisting of
a 5 membered heteroaryl group optionally substituted in the carbon skeleton by a fluorine, chlorine or bromine atom, by a methyl or methoxy group, while the 5-membered heteroaryl group contains an oxygen or sulphur atom, and a phenyl ring fused to the abovementioned monocyclic heteroaryl groups via two adjacent carbon atoms, by means of which the bicyclic heteroaryl group is linked to the $R_1$ substituted alkene-carbon atom and which may also be substituted in the carbon skeleton by a fluorine, chlorine or bromine atom or by a methyl or methoxy group, an isomer thereof or a salt thereof.

4. The carboxylic acid snide according to claim 1, wherein $R_1$ is a hydrogen atom or a $C_{1-3}$-alkyl group, $R_2$ is a hydrogen atom or a methyl group, $R_3$ is a hydrogen atom, A is a benzofuryl or benzothienyl group bound via the phenyl moiety to the $R_1$-substituted alkene-carbon atom and optionally substituted by a methyl group and B is a phenyl group substituted by a carboxy, methoxycarbonyl or ethoxycarbonyl group, which may additionally be substituted by a fluorine, chlorine or bromine atom,
by a methyl, trifluoromethyl, phenyl, hydroxymethyl, hydroxy, methoxy, 2-dimethylamino-ethoxy, nitro, methylsulphonylamino, phenylsulphonylamino, aminosulphonyl, pyrrolidino, piperidino or morpholino group,
by an amino, N-methyl-amino or N-(2-methoxy-ethyl)-amino group which may be substituted in each case at the amino-nitrogen atom by a $C_{1-3}$-alkyl group,
or by an aminocarbonyl, methylaminocarbonyl or dimethylaminocarbonyl group,
whilst the abovementioned phenyl groups may additionally be substituted by another fluorine or chlorine atom or by another methyl or methoxy group,
an isomer thereof or a salt thereof.

5. The carboxylic acid amide according to claim 1, wherein
$R_1$ is a hydrogen atom, a methyl or ethyl group,
$R_2$ is a hydrogen atom,
$R_3$ is a hydrogen atom,
A is a benzothienyl group bound to the $R_1$-substituted alkene-carbon atom via the phenyl moiety and optionally substituted by a methyl group and
B is a phenyl group substituted in each case by a carboxy group, while the abovementioned phenyl group may additionally be substituted
by a fluorine, chlorine or bromine atom,
by a methyl, hydroxy, $C_{1-3}$-alkoxy, pyrrolidino, piperidino, morpholino or N—($C_{1-3}$-alkyl)-piperazino group,
by a 2-dimethylaminoethoxy group,
by an amino, methylamino or dimethylamino group or
by an aminocarbonyl, methylaminocarbonyl or dimethylaminocarbonyl group and
the disubstituted phenyl groups may additionally be substituted by another fluorine atom or by another methyl or methoxy group,
an isomer thereof or a salt thereof.

6. The carboxylic acid amide according to claim 1, wherein
$R_1$ is a methyl group,
$R_2$ is a hydrogen atom,
$R_3$ is a hydrogen atom,
A is a benzothienyl group bound to the $R_1$-substituted alkene-carbon atom via the phenyl moiety and
B is a 2-carboxy-phenyl group, while the abovementioned 2-carboxy-phenyl group may additionally be substituted in the phenyl nucleus
by a fluorine, chlorine or bromine atom,
by a methyl, hydroxy, $C_{1-3}$-alkoxy, amino, methylamino, dimethylamino or morpholino group,
by a 2-dimethylaminoethoxy group or
by an aminocarbonyl, methylaminocarbonyl or dimethylaminocarbonyl group and optionally additionally by another fluorine atom or by another methoxy group,
an isomer thereof or a salt thereof.

7. The carboxylic amide according to claim 1:
(1) trans-3-(benzothien-6-yl)-but-2-enoic acid-N-(2-carboxy-phenyl)-amide,
(2) trans-3-(benzothien-5-yl)-but-2-enoic acid-N-(2-carboxy-phenyl)-amide,
(3) trans-3-(benzothien-6-yl)-but-2-enoic acid-N-(2-carboxy-4,5-dimethoxyphenyl)-amide,
(4) trans-3-(benzothien-6-yl)-but-2-enoic acid-N-(2-carboxy-6-methylphenyl)-amide, or
(5) trans-3-(benzothien-6-yl)-but-2-enoic acid-N-(2-carboxy-4-fluorophenyl)-amide;
or salt thereof.

8. The carboxylic acid amide according to claim 1, characterized in that said carboxylic add amide is in the form of a physiologically acceptable salt.

9. A pharmaceutical composition comprising a carboxylic amide according to claim 1 together with one or more inert carriers or diluents.

10. A method for treating disease in a warm-blooded animal, which disease involves an excess production of telomerase which comprises administering to the animal a therepeutically effective dose of a carboxylic amide according to claim 1.

* * * * *